US009630909B2

(12) United States Patent
Sonny et al.

(10) Patent No.: US 9,630,909 B2
(45) Date of Patent: Apr. 25, 2017

(54) PROCESS FOR THE PREPARATION OF NEPAFENAC

(71) Applicant: Mylan Laboratories Ltd., Jubilee Hills (IN)

(72) Inventors: Sebastian Sonny, Hyderabad (IN); Rao Jagadeeshwar, Hyderabad (IN); Srinivas Rao Mannava, Hyderabad (IN); Suresh Reddy Sabbella, Hyderabad (IN)

(73) Assignee: Mylan Laboratories Ltd, Jubilee Hills, Hyderbad (IN)

( * ) Notice: Subject to any disclaimer, the term of this patent is extended or adjusted under 35 U.S.C. 154(b) by 0 days.

(21) Appl. No.: 14/998,555

(22) PCT Filed: Jun. 26, 2014

(86) PCT No.: PCT/IN2014/000429
§ 371 (c)(1),
(2) Date: Dec. 24, 2015

(87) PCT Pub. No.: WO2014/207769
PCT Pub. Date: Dec. 31, 2014

(65) Prior Publication Data
US 2016/0214927 A1    Jul. 28, 2016

(30) Foreign Application Priority Data

Jun. 27, 2013  (IN) .......................... 2823/CHE/2013
Nov. 4, 2013   (IN) .......................... 4979/CHE/2013

(51) Int. Cl.
*C07C 231/12* (2006.01)
*C07C 231/24* (2006.01)
*C07C 319/14* (2006.01)
*C07C 319/20* (2006.01)

(52) U.S. Cl.
CPC .......... *C07C 231/12* (2013.01); *C07C 231/24* (2013.01); *C07C 319/14* (2013.01); *C07C 319/20* (2013.01)

(58) Field of Classification Search
CPC ... C07C 231/12; C07C 231/24; C07C 319/14; C07C 319/20
See application file for complete search history.

(56) References Cited

U.S. PATENT DOCUMENTS

| | | | |
|---|---|---|---|
| 5,475,034 A | 12/1995 | Yanni et al. | |
| 6,066,671 A | 5/2000 | Yanni et al. | |
| 6,174,878 B1 | 1/2001 | Gamache et al. | |
| 6,342,524 B1 | 1/2002 | Hellberg et al. | |
| 6,395,746 B1 | 5/2002 | Cagle et al. | |
| 6,403,609 B1 | 6/2002 | Asgharian | |
| 6,551,584 B2 | 4/2003 | Bandyopadhyay et al. | |
| 6,638,976 B2 | 10/2003 | Gamache et al. | |
| 6,646,001 B2 | 11/2003 | Hellberg et al. | |
| 6,646,003 B2 | 11/2003 | Graff et al. | |
| 6,716,830 B2 | 4/2004 | Cagle et al. | |
| 6,740,664 B2 | 5/2004 | Cagle et al. | |
| 7,736,624 B2 | 6/2010 | Marnett et al. | |
| 7,741,359 B2 | 6/2010 | Wallace et al. | |
| 7,758,778 B2 | 7/2010 | Persyn et al. | |
| 7,820,195 B2 | 10/2010 | Kauper et al. | |
| 7,834,059 B2 | 11/2010 | Wong | |
| 7,947,295 B2 | 5/2011 | Chowhan et al. | |
| 7,964,738 B2 | 6/2011 | Gately et al. | |
| 8,071,648 B2 | 12/2011 | Wong | |
| 8,278,484 B2 | 10/2012 | Suárez et al. | |
| 8,324,281 B2 | 12/2012 | Wong | |
| 2002/0022629 A1 | 2/2002 | Cagle et al. | |
| 2002/0035264 A1 | 3/2002 | Kararli et al. | |
| 2002/0037929 A1 | 3/2002 | Kapin et al. | |
| 2002/0049255 A1 | 4/2002 | Gamache et al. | |
| 2002/0103255 A1 | 8/2002 | Hellberg et al. | |
| 2002/0107238 A1 | 8/2002 | Bandyopadhyay et al. | |
| 2002/0183376 A1 | 12/2002 | Graff et al. | |
| 2002/0193370 A1 | 12/2002 | Cagle et al. | |
| 2003/0187072 A1 | 10/2003 | Kapin et al. | |
| 2003/0207941 A1 | 11/2003 | Bingaman et al. | |
| 2004/0132773 A1 | 7/2004 | Gamache et al. | |
| 2004/0219220 A1 | 11/2004 | Sherry et al. | |
| 2004/0224010 A1 | 11/2004 | Hofland et al. | |
| 2004/0259765 A1 | 12/2004 | Bingaman | |
| 2005/0143468 A1 | 6/2005 | Bingaman et al. | |
| 2005/0187241 A1 | 8/2005 | Wen et al. | |

(Continued)

FOREIGN PATENT DOCUMENTS

AU    199916259    7/1999
AU    2005311738   6/2006

(Continued)

OTHER PUBLICATIONS

Savall et al, J. Org. Chem., 61, No. 24, 1996, 8696-97.*
Marcin et al, Letters in Organic Chemistry, vol. 9, No. 7, 2012, 461-64(see the abstract only).*
P.G. Gassman & G. Gruetzmacher, "Specific Ortho Alkylation of Aromatic Amines" Jan. 24, 1973; 95(2): 588-89.
P.G. Gassman et al., "Use of Halogen-Sulfide Complexes in the Synthesis of Indoles, Oxindoles, and Alkylated Aromatic Amines" Sep. 19, 1973; 95(19): 6508-09.

*Primary Examiner* — Shailendra Kumar

(57) ABSTRACT

Described herein are processes for the preparation of nepafenac and related intermediates, particularly wherein 2-aminobenzophenone is treated with a 2-(alkylthio)acetamide in the presence of sulfuryl chloride to afford a 2-(2-amino-3-benzoyl-phenyl)-2-(alkylthio)acetamide, which upon reduction affords nepafenac. Described herein are also processes for the purification of nepafenac, particularly for the removal of structurally similar impurities.

20 Claims, No Drawings

(56) References Cited

U.S. PATENT DOCUMENTS

| | | |
|---|---|---|
| 2006/0100288 A1 | 5/2006 | Bague et al. |
| 2006/0257487 A1 | 11/2006 | Owen et al. |
| 2007/0043006 A1 | 2/2007 | Bingaman |
| 2007/0048373 A1 | 3/2007 | Chastain et al. |
| 2007/0116729 A1 | 5/2007 | Palepu |
| 2007/0166402 A1 | 7/2007 | Friedlaender et al. |
| 2007/0248645 A1 | 10/2007 | Bague et al. |
| 2007/0254841 A1 | 11/2007 | Ousler, III et al. |
| 2007/0297981 A1 | 12/2007 | Ousler, III et al. |
| 2007/0299124 A1 | 12/2007 | Ousler, III et al. |
| 2008/0031903 A1 | 2/2008 | Gambotto et al. |
| 2008/0038316 A1 | 2/2008 | Wong et al. |
| 2008/0039398 A1 | 2/2008 | Ousler, III et al. |
| 2008/0107738 A1 | 5/2008 | Philips et al. |
| 2008/0220079 A1 | 9/2008 | Chen et al. |
| 2008/0233053 A1 | 9/2008 | Gross et al. |
| 2008/0268020 A1 | 10/2008 | Philips et al. |
| 2009/0010850 A1 | 1/2009 | Ousler, III et al. |
| 2009/0018057 A1 | 1/2009 | Lambert et al. |
| 2009/0028955 A1 | 1/2009 | Philips et al. |
| 2009/0105245 A1 | 4/2009 | Bingaman |
| 2009/0111780 A1 | 4/2009 | Girodano |
| 2009/0136514 A1 | 5/2009 | Power |
| 2009/0209574 A1 | 8/2009 | Owen et al. |
| 2009/0312429 A1 | 12/2009 | Safanova et al. |
| 2009/0312575 A1 | 12/2009 | Suarez et al. |
| 2010/0093673 A1 | 4/2010 | Oronsky |
| 2010/0144719 A1 | 6/2010 | Kabra |
| 2010/0166874 A1 | 7/2010 | Malakhov et al. |
| 2010/0172969 A1 | 7/2010 | Dreu et al. |
| 2010/0172998 A1 | 7/2010 | Mathiowitz et al. |
| 2010/0173876 A1 | 7/2010 | Lichtenberger et al. |
| 2010/0183502 A1 | 7/2010 | Anderson |
| 2010/0184946 A1 | 7/2010 | Van Boxtel |
| 2010/0226997 A1 | 9/2010 | Bowman et al. |
| 2010/0234469 A1 | 9/2010 | Gavaldá Escudé et al. |
| 2010/0331430 A1 | 12/2010 | Olejnik |
| 2011/0015271 A1 | 1/2011 | Wong |
| 2011/0021443 A1 | 1/2011 | Lambert et al. |
| 2011/0129516 A1 | 6/2011 | Jacob et al. |
| 2011/0135743 A1 | 6/2011 | Chowhan et al. |
| 2012/0027716 A1 | 2/2012 | Stein et al. |
| 2012/0029084 A1 | 2/2012 | Wong |

FOREIGN PATENT DOCUMENTS

| | | |
|---|---|---|
| AU | 2006244244 | 11/2006 |
| CA | 2313386 | 7/1999 |
| CA | 2414780 | 1/2002 |
| CA | 2417282 | 2/2002 |
| CA | 2418059 | 2/2002 |
| CA | 2167524 | 8/2002 |
| CA | 2483275 | 11/2003 |
| CA | 2498191 | 4/2004 |
| CA | 2527121 | 12/2004 |
| CA | 2581126 | 4/2006 |
| CA | 2578176 | 5/2006 |
| CA | 2586074 | 5/2006 |
| CA | 2607608 | 11/2006 |
| CA | 2625568 | 4/2007 |
| CA | 2628178 | 5/2007 |
| CA | 2632568 | 6/2007 |
| CA | 2672377 | 7/2008 |
| CA | 2745123 | 6/2010 |
| EP | 0716600 | 4/2002 |
| EP | 1655021 | 5/2006 |
| EP | 1929996 | 6/2008 |
| EP | 1967212 | 9/2008 |
| EP | 2123626 | 11/2009 |
| EP | 2144599 | 8/2010 |
| EP | 2016936 | 9/2010 |
| WO | 99/32104 | 7/1999 |
| WO | 01/15678 | 3/2001 |
| WO | 02/05815 | 1/2002 |
| WO | 02/13804 | 2/2002 |
| WO | 02/13805 | 2/2002 |
| WO | 03/092669 | 11/2003 |
| WO | 2004/022939 | 3/2004 |
| WO | 2004/027027 | 4/2004 |
| WO | 2004/112772 | 12/2004 |
| WO | 2006/037106 | 4/2006 |
| WO | 2006/050836 | 5/2006 |
| WO | 2006/050837 | 5/2006 |
| WO | 2006/050838 | 5/2006 |
| WO | 2006/060618 | 6/2006 |
| WO | 2006/082588 | 8/2006 |
| WO | 2006/121963 | 11/2006 |
| WO | 2007/042262 | 4/2007 |
| WO | 2007/061529 | 5/2007 |
| WO | 2007/067807 | 6/2007 |
| WO | 2007/070463 | 6/2007 |
| WO | 2007/087609 | 8/2007 |
| WO | 2008/014431 | 1/2008 |
| WO | 2008/084171 | 7/2008 |
| WO | 2008/153746 | 12/2008 |
| WO | 2009/007409 | 1/2009 |
| WO | 2009/059191 | 5/2009 |
| WO | 2009/103053 | 8/2009 |
| WO | 2009/105534 | 8/2009 |
| WO | 2009/141144 | 11/2009 |
| WO | 2009/150524 | 12/2009 |
| WO | 2009/151619 | 12/2009 |
| WO | 2011/053841 | 5/2011 |
| WO | 2011/068872 | 6/2011 |
| WO | 2011/084473 | 7/2011 |
| WO | 2011/098578 | 8/2011 |
| WO | 2011/106702 | 9/2011 |
| WO | 2011/109732 | 9/2011 |
| WO | 2012/009696 | 1/2012 |

\* cited by examiner

PROCESS FOR THE PREPARATION OF NEPAFENAC

CROSS-REFERENCE TO RELATED APPLICATIONS

This application is a national stage filing of PCT application no. PCT/IN2014/000429, filed Dec. 31, 2014, which in turn claimed priority to and the benefit of priority to IN2823/CHE/2013, filed on Jun. 27, 2013, and IN4979/CHE/2013, filed on Nov. 4, 2013.

FIELD

Processes for the preparation of nepafenac and intermediates thereof, as well as processes for the purification of nepafenac.

DESCRIPTION OF THE RELATED ART

Nepafenac is a non-steroidal anti-inflammatory drug (NSAID) approved for ophthalmic use. Nepafenac is sometimes referred to as 2-amino-3-benzoylbenzeneacetamide and is structurally represented by Formula (I).

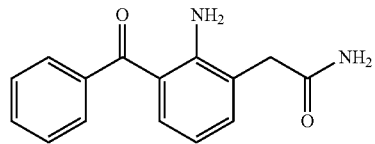

Formula (I)

U.S. Pat. No. 4,313,949 discloses nepafenac and its preparation by treating 2-aminobenzophenone (II) with 2-(methylthio)acetamide (III) in the presence of t-butylhypochlorite to afford 2-(2-amino-3-benzoylphenyl)-2-(methylthio)acetamide (IV), which is subsequently reduced in the presence of Raney nickel and crystallized from isopropyl alcohol to afford nepafenac. This process is represented below in Scheme I.

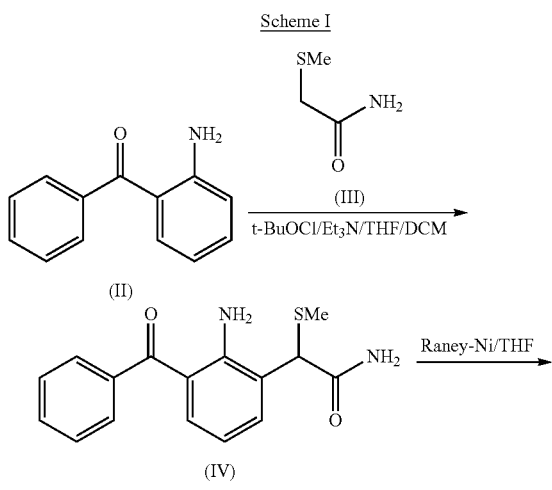

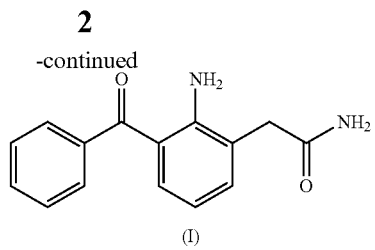

(I)

U.S. Pat. No. 8,278,484 discloses a process for the preparation of nepafenac in which 2-aminobenzophenone (II) is treated with 2-(methylthio)acetamide (III) in the presence of N-chlorosuccinimide to afford 2-(2-amino-3-benzoylphenyl)-2-(methylthio)acetamide (IV), which is subsequently reduced in the presence of Raney nickel to afford nepafenac. This process is represented below in Scheme II.

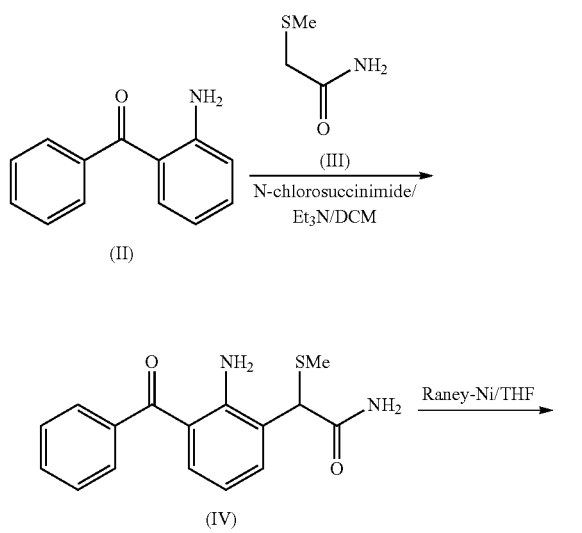

Indian Publication No. 148/MUM/2011 discloses a process for the preparation of nepafenac in which 2-aminobenzophenone (II) is treated with 2-(methylthio)acetamide (III) in the presence of N-chlorophthalimide to afford 2-(2-amino-3-benzoylphenyl)-2-(methylthio)acetamide (IV), which is subsequently reduced in the presence of Raney nickel under hydrogen pressure to afford nepafenac.

A structurally similar impurity is also formed during the preparation of nepafenac. This impurity is known as 2-amino-3-benzoyl-5-chlorobenzeneacetamide and is represented below by Formula (Ia).

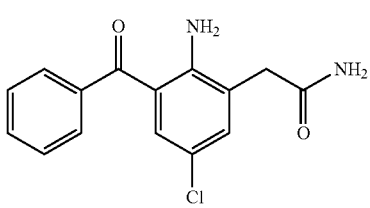

Formula (Ia)

2-Amino-3-benzoyl-5-chlorobenzene acetamide

This impurity is difficult to remove by conventional purification methods. Moreover, U.S. Pat. No. 8,278,484 describes this impurity as causing "reproducibility problems" during the synthesis of nepafenac and also characterizes the formation of this impurity as a "drawback" suffered by the synthesis described in U.S. Pat. No. 4,313,949. Accordingly, there is a continuing need for new and improved processes for the preparation of nepafenac, as well as methods for removing, reducing, or eliminating the chlorinated impurities formed during the preparation of nepafenac from nepafenac compositions.

SUMMARY OF THE DISCLOSURE

Some aspects of the present disclosure are to provide a process for the preparation of nepafenac.

One aspect provides a process for the preparation of 2-(2-amino-3-benzoylphenyl)-2-(methylthio)acetamide (IV), comprising: treating 2-aminobenzophenone (II) with 2-(methylthio)acetamide (III) in the presence of sulfuryl chloride to afford 2-(2-amino-3-benzoylphenyl)-2-(methylthio)acetamide (IV).

One aspect provides a process for the preparation of nepafenac, comprising:
  a) treating 2-aminobenzophenone (II) with 2-(methylthio) acetamide (III) in the presence of sulfuryl chloride and a base to afford 2-(2-amino-3-benzoylphenyl)-2-(methylthio)acetamide (IV), and
  b) removing the thiomethyl moiety from the 2-(2-amino-3-benzoylphenyl)-2-(methylthio)acetamide (IV) to afford nepafenac.

In some embodiments, the removing of the thiomethyl moiety is conducted under reducing conditions. In some embodiments, the reducing conditions comprise hydrogen gas and a catalyst. In some embodiments, the catalyst is Raney nickel, palladium on carbon, palladium oxide, or platinum oxide. In some embodiments, the catalyst is Raney nickel. In some embodiments, the catalyst is palladium on carbon. In some embodiments, the catalyst is platinum oxide. In some embodiments, the catalyst is palladium oxide. In some embodiments, the reducing conditions further comprise a solvent selected from the group consisting of diethyl ether, tetrahydrofuran, and diisopropylether. In some embodiments, the base is a trialkylamine, a dialkylamine, a cycloamine, or an N-alkylcycloamine. In some embodiments, the base is selected from the group consisting of: triethylamine, diisopropylamine, methylisopropylamine, N-methylmorpholine and mixtures thereof. In some embodiments, the base is triethylamine. In some embodiments, the base is diisopropylethylamine. In some embodiments, the treating of 2-aminobenzophenone (II) with 2-(methylthio) acetamide (III) occurs in a solvent selected from the group consisting of dichloromethane, dichloroethane, chloroform, diethyl ether, tetrahydrofuran, diisopropylether and mixtures thereof.

Some embodiments are directed to a process for the purification of a nepafenac composition containing a halogenated impurity, comprising: subjecting a nepafenac composition containing a halogenated impurity to reducing conditions, wherein the reducing conditions convert the halogenated impurity to nepafenac, and optionally crystallizing the resultant nepafenac composition. In some embodiments, the halogenated impurity is 2-amino-3-benzoyl-5-chlorobenzeneacetamide. In some embodiments, the reducing conditions comprise hydrogen gas and a catalyst. In some embodiments, the catalyst is Raney nickel, palladium on carbon, palladium oxide, or platinum oxide. In some embodiments, the reducing conditions further include a base. In some embodiments, the base is selected from the group consisting of sodium hydroxide, potassium hydroxide, sodium carbonate, potassium carbonate, diisopropylamine, methylisopropylamine and triethylamine. In some embodiments, the resultant nepafenac composition is crystallized and the crystallization is performed in a solvent comprising an alcohol. In some embodiments, the alcohol is methanol, ethanol, isopropanol or mixtures thereof. In some embodiments, the resultant nepafenac is crystallized from an isopropanol-water (9:1) mixture.

Some embodiments are directed to a process for the preparation of 2-(2-amino-3-benzoylphenyl)-2-(methylthio) acetamide (IV), comprising: treating 2-aminobenzophenone (II) with 2-(methylthio)acetamide (III) in the presence of sulfuryl chloride and a base to afford 2-(2-amino-3-benzoylphenyl)-2-(methylthio)acetamide (IV). In some embodiments, the base is a trialkylamine, a dialkylamine, a cycloamine, or an N-alkylcycloamine. In some embodiments, the treating occurs at about –30° C.

Some embodiments are directed to a process for the preparation of nepafenac, comprising:
  a) treating 2-aminobenzophenone (II) with 2-(methylthio) acetamide (III) in the presence of sulfuryl chloride and a base to afford 2-(2-amino-3-benzoylphenyl)-2-(methylthio)acetamide (IV);
  b) removing the thiomethyl moiety from the 2-(2-amino-3-benzoylphenyl)-2-(methylthio)acetamide (IV) to afford a nepafenac composition containing a halogenated impurity;
  c) subjecting the nepafenac composition containing the halogenated impurity to reducing conditions, wherein the reducing conditions convert the halogenated impurity to nepafenac; and
  d) optionally crystallizing the resultant nepafenac composition.

Some embodiments are directed to a process for the preparation of nepafenac, comprising:
  a) treating 2-aminobenzophenone (II) with 2-(methylthio) acetamide (III) in the presence of sulfuryl chloride to afford 2-(2-amino-3-benzoylphenyl)-2-(methylthio)acetamide (IV), and
  b) removing the thiomethyl moiety from the 2-(2-amino-3-benzoylphenyl)-2-(methylthio)acetamide (IV) to afford nepafenac.

Some embodiments are directed to a process for the preparation of nepafenac, comprising:
  a) treating 2-aminobenzophenone (II) with 2-(methylthio) acetamide (III) in the presence of sulfuryl chloride to afford 2-(2-amino-3-benzoylphenyl)-2-(methylthio)acetamide (IV), and
  b) reducing the 2-(2-amino-3-benzoylphenyl)-2-(methylthio)acetamide (IV) to afford nepafenac.

Some embodiments are directed to a process for the purification of a nepafenac composition containing a halogenated impurity, comprising: subjecting a nepafenac composition containing a halogenated impurity to reducing conditions, wherein the reducing conditions convert the halogenated impurity to nepafenac.

Some embodiments are directed to a process for the purification of a nepafenac composition containing a chlorinated impurity, comprising: hydrogenating a nepafenac composition containing a chlorinated impurity, wherein the hydrogenating converts the chlorinated impurity to nepafenac.

Some embodiments are directed to a process for the purification of a nepafenac composition containing a chlorinated impurity, comprising:
a) hydrogenating a nepafenac composition containing a chlorinated impurity, wherein the hydrogenating converts the chlorinated impurity to nepafenac, and
b) optionally crystallizing the step a) product in an alcohol and water solvent to afford nepafenac.

Some embodiments are directed to a process for the purification of a nepafenac composition containing a chlorinated impurity, comprising:
a) hydrogenating a nepafenac composition containing a chlorinated impurity in the presence of a catalyst and a base,
b) optionally crystallizing the step a) product in an alcohol and water solvent, and isolating pure nepafenac.

Scheme III below represents other embodiments in the present disclosure.

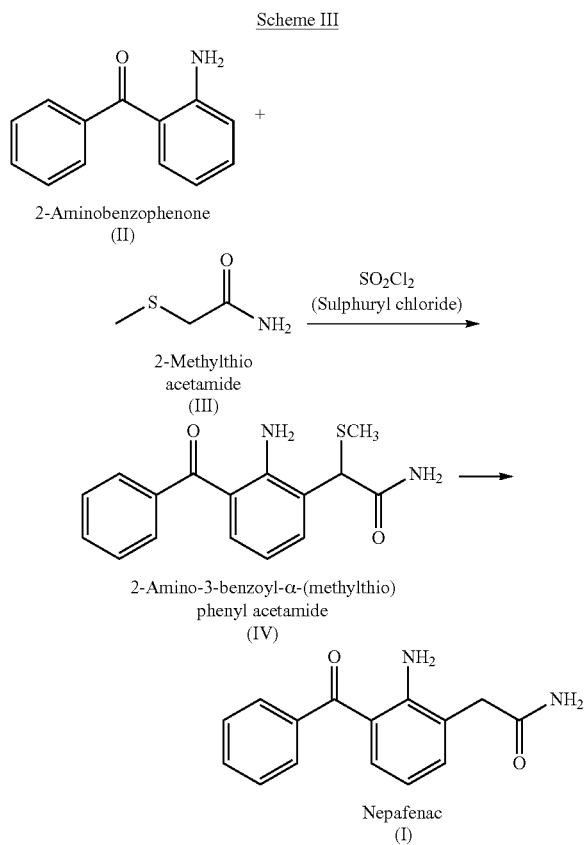

DETAILED DESCRIPTION OF THE DISCLOSURE

The present disclosure is directed to a process for the preparation of nepafenac, wherein 2-aminobenzophenone of Formula (II) is treated with 2-(methylthio)acetamide of Formula (III) in the presence of sulfuryl chloride to yield 2-(2-amino-3-benzoylphenyl)-2-(methylthio)acetamide of Formula (IV), which upon reduction affords nepafenac, represented by Formula (I). See, e.g., Scheme III above.

The present disclosure also relates to a process for the purification of nepafenac to remove a structurally similar impurity, wherein the nepafenac containing the structurally similar impurity compound is subjected to hydrogenation in the presence of a catalyst and a base, followed by isolation, to afford nepafenac. The obtained nepafenac of formula (I) is optionally subjected to crystallization in a mixture of alcohol and water to obtain a purified nepafenac. In some embodiments, the structurally similar impurity is a halogenated impurity, particularly one which contains a halogenated aromatic ring. In some embodiments, the halogenated impurity is 2-amino-3-benzoyl-5-chlorobenzeneacetamide.

One embodiment of the present disclosure is to provide an improved process for the preparation of nepafenac comprising the steps of:
a) reacting 2-aminobenzophenone of Formula (II) with 2-(methylthio)acetamide of Formula (III) in the presence of sulfuryl chloride to afford a 2-(2-amino-3-benzoylphenyl)-2-(methylthio)acetamide (IV), and
b) reducing the compound of formula (IV) to obtain nepafenac.

The reaction of 2-aminobenzophenone of Formula (II) with 2-(methylthio)acetamide of Formula (III) is carried out in the presence of sulfuryl chloride and a base, preferably an organic base in a chlorinated solvent, at a temperature in the range of about −40° to about 0° C., preferably about −30° C., for a period of about 30 minutes to about 2 hours to afford a 2-(2-amino-3-benzoylphenyl)-2-(methylthio)acetamide of formula (IV). The 2-(2-amino-3-benzoylphenyl)-2-(methylthio)acetamide of formula (IV) is then reduced in the presence of a catalyst under hydrogen pressure in a suitable solvent, such as an ether and water solvent, at a temperature in the range of about 20° C. to about 35° C. and the reaction mixture is stirred for a period of 10 minutes to 60 minutes to afford nepafenac of formula (I). One of skill in the art will readily understand that a 2-(alkylthio)acetamide may be utilized in place of the specifically exemplified 2-(methylthio)acetamide. Moreover, a skilled artisan will readily recognize that alternative sources of hydrogen may be utilized in place of hydrogen gas in the reduction reaction described above. Such alternative sources include, but are not limited to, hydrazine, dihydronapthalene, dihydroanthracene, isopropanol, formic acid, and the like. Alternative hydrogen sources for reduction reactions are well-known in the synthetic arts.

According to the present disclosure, the base that is utilized in the reaction of 2-aminobenzophenone of Formula (II) with 2-(methylthio)acetamide of Formula (III) in the presence of sulfuryl chloride may be selected form organic amines such as trialkylamines, dialkylamines, monoalkylamines, cycloamines, and N-alkylcycloamines. As used herein, "alkyl" refers to $C_1$-$C_6$ linear and branched alkyl groups. As used herein, "cycloamine" refers to dialkylamines in which two of the alkyl groups are taken together to form a nitrogen-containing heterocyle (such as morpholine, piperidine, piperazine, pyrrolidine, imidazole, and pyridine). Non-limiting examples of trialkylamines include triethylamine and diisopropylethylamine. Non-limiting examples of dialkylamines include diisopropylamine and methylisopropylamine. Non-limiting examples of N-alkylcycloamines include N-methylmorpholine, N,N-dimethylpiperazine, N-methylpiperazine, and N-methylpyrollidine. A skilled artisan will readily understand that mixtures of the aforementioned bases can be utilized.

According to the present disclosure, the solvent for the reaction of 2-aminobenzophenone of Formula (II) with 2-(methylthio)acetamide of Formula (III) in the presence of sulfuryl chloride may be selected from chlorinated solvents such as dichloromethane (or "DCM"), dichloroethane, or chloroform, as well as ether solvents such as diethyl ether, tetrahydrofuran or diisopropylether. Additional solvents include those suitable for aromatic acylation reactions.

According to the present disclosure, the catalyst for the reduction of 2-(2-amino-3-benzoylphenyl)-2-(methylthio) acetamide may be a metal catalyst such as Raney nickel, Palladium on carbon, Palladium oxide, or Platinum oxide. The solvent used in the reduction of 2-(2-amino-3-benzoylphenyl)-2-(methylthio)acetamide may be selected from an ether solvent such as without limitation, diethyl ether, tetrahydrofuran, or diisopropylether. Other solvents include those that are compatible with catalytic reductions, mixtures thereof, and aqueous mixtures thereof. Such solvents include, but are not limited to, alcohols exemplified by methanol, ethanol, isopropanol and n-butanol.

Another embodiment of the present disclosure relates to an improved process for the purification of nepafenac containing the structurally similar impurity comprising the steps of:
  a) hydrogenating nepafenac containing 2-amino-3-benzoyl-5-chlorobenzeneacetamide as a chlorinated impurity in the presence of a catalyst and a base;
  b) optionally crystallizing the step a) product in a mixture of alcohol and water solvent; and
  c) isolating nepafenac.

According to the present disclosure, impure nepafenac, which is containing 2-amino-3-benzoyl-5-chlorobenzene acetamide as a halogenated impurity in the range of, for example, about 0.3% to about 0.7%, is hydrogenated in the presence of a catalyst and a base in a solvent at about 40-45° C. under 5-7 psi hydrogen pressure until effective reaction completion, or for about about 6-15 hours, about 8-10 hours, or about 12-13 hours. After the effective completion of the reaction, the catalyst is filtered and the filtrate is concentrated to afford nepafenac. This is then optionally subjected to further purification by crystallization from an appropriate solvent. Crystallization solvents include, but are not limited to, alcohols such as methanol, ethanol, isopropanol, n-butanol, or mixtures thereof, as well as alcohol-water mixtures. A 9:1 ratio of alcohol to water has proven useful in practice, with 9:1 isopropanol:water being particularly preferred.

According to the present disclosure, the catalyst for use during the removal of the halogenated impurity may be selected from metal catalyst such as without limitation, palladium on carbon, or platinum oxide. Palladium on carbon is particularly preferred. The base for use during the removal of the halogenated impurity is one that is suitable for use during catalytic reductions, and may be selected without limitation from bases such as sodium hydroxide, potassium hydroxide, sodium carbonate, potassium carbonate, diisopropylamine, methylisopropylamine and triethylamine. Organic amines such as trialkylamines, dialkylamines, monoalkylamines, cycloalkylamines, and N-alkylcycloamines as previously described above are particularly preferred. Moreover, a skilled artisan will readily recognize that alternative sources of hydrogen as described above may be utilized in place of hydrogen gas in the reduction reaction.

According to the present disclosure, the solvent for for use during the removal of the halogenated impurity includes, but is not limited to those that are suitable for use during catalytic reductions. These include alcohols such as methanol, ethanol, isopropanol and n-butanol, ethers such as diethyl ether and tetrahydrofuran, and esters such as ethyl acetate.

Additional Aspects of the Detailed Disclosure

Additional aspects of the detailed disclosure are repeated and further enumerated as follows:
1. A process for the preparation of nepafenac, comprising:
    a) treating 2-aminobenzophenone (II) with 2-(methylthio)acetamide (III) in the presence of sulfuryl chloride and a base to afford 2-(2-amino-3-benzoylphenyl)-2-(methylthio)acetamide (IV), and
    b) removing the thiomethyl moiety from the 2-(2-amino-3-benzoylphenyl)-2-(methylthio)acetamide (IV) to afford nepafenac.
2. A process for the preparation of nepafenac, comprising:
    a) treating 2-amino-benzophenone (II) with 2-(methylthio)acetamide (III) in the presence of sulfuryl chloride and a base to afford 2-(2-amino-3-benzoylphenyl)-2-(methylthio)acetamide (IV);
    b) removing the thiomethyl moiety from the 2-(2-amino-3-benzoylphenyl)-2-(methylthio)acetamide (IV) to afford a nepafenac composition containing a halogenated impurity;
    c) subjecting the nepafenac composition containing the halogenated impurity to reducing conditions, wherein the reducing conditions convert the halogenated impurity to nepafenac; and
    d) optionally crystallizing the resultant nepafenac composition.
3. A process for the purification of a nepafenac composition containing a halogenated impurity, comprising: subjecting a nepafenac composition containing a halogenated impurity to reducing conditions, wherein the reducing conditions convert the halogenated impurity to nepafenac, and optionally crystallizing the resultant nepafenac composition.
4. A process for the preparation of 2-(2-amino-3-benzoylphenyl)-2-(methylthio)acetamide (IV), comprising: treating 2-aminobenzophenone (II) with 2-(methylthio)acetamide (III) in the presence of sulfuryl chloride and a base to afford 2-(2-amino-3-benzoylphenyl)-2-(methylthio)acetamide (IV).
5. The process of any one of aspects 1-4, wherein the removing of the thiomethyl moiety is conducted under reducing conditions.
6. The process of any one of aspects 1-5, wherein the reducing conditions comprise a hydrogen source and a catalyst.
7. The process of any one of aspects 1-6, wherein the catalyst is Raney nickel, palladium on carbon, palladium oxide, or platinum oxide.
8. The process of any one of aspects 1-7, wherein the reducing conditions further comprise a solvent selected from the group consisting of diethyl ether, tetrahydrofuran, and diisopropylether.
9. The process of any one of aspects 1-8, wherein the hydrogen source is hydrogen gas.

10. The process of any one of aspects 1-9, wherein the base is a trialkylamine, a dialkylamine, a cycloalkylamine, or an N-alkylcycloamine.
11. The process of any one of aspects 1-10, wherein the base is selected from the group consisting of: triethylamine, diisopropylamine, methylisopropylamine, N-methylmorpholine and mixtures thereof.
12. The process of any one of aspects 1-11, wherein the treating of 2-aminobenzophenone (II) with 2-(methylthio)acetamide (III) occurs in a solvent selected from the group consisting of dichloromethane, dichloroethane, chloroform, diethyl ether, tetrahydrofuran, diisopropylether and mixtures thereof.
13. The process of any one of aspects 1-12, wherein the halogenated impurity is 2-amino-3-benzoyl-5-chlorobenzeneacetamide.
14. The process of any one of aspects 1-13, wherein the reducing conditions further include a base.
15. The process of any one of aspects 1-14, wherein the base is selected from the group consisting of sodium hydroxide, potassium hydroxide, sodium carbonate, potassium carbonate, diisopropylamine, methylisopropylamine and triethylamine and the hydrogen source is hydrogen gas.
16. The process of any one of aspects 1-15, wherein the resultant nepafenac composition is crystallized and the crystallization is performed in a solvent comprising an alcohol.
17. The process of any one of aspects 1-16, wherein the alcohol is methanol, ethanol, isopropanol or mixtures thereof.
18. The process of any one of aspects 1-17, wherein the resultant nepafenac is crystallized from an isopropanol-water (9:1) mixture.
19. The process of any one of aspects 1-18, wherein treating the 2-aminobenzophenone (II) with the 2-(methylthio)acetamide (III) in the presence of sulfuryl chloride and a base is conducted at a temperature between −40° C. and 0° C.
20. The process of any one of aspects 1-19, wherein treating the 2-aminobenzophenone (II) with the 2-(methylthio)acetamide (III) in the presence of sulfuryl chloride and a base is conducted at a temperature of about −30° C.

EXAMPLES

In view of the above description and the examples below, one of ordinary skill in the art will be able to practice the invention as claimed without undue experimentation. The foregoing will be better understood with reference to the following examples that detail certain procedures for the preparation of molecules, compositions and formulations according to the present invention. All references made to these examples are for the purposes of illustration. The following examples should not be considered exhaustive, but merely illustrative of only a few of the many aspects and embodiments contemplated by the present disclosure.

Example-1

Preparation of 2-amino-3-benzoyl-α-(methylthio) phenylacetamide (also referred to as 2-(2-amino-3-benzoylphenyl)-2-(methylthio)acetamide)

To a suspension of 2-aminobenzophenone (75 g) and 2-(methylthio)acetamide (22 g) in methylene dichloride (450 mL) was added dropwise a solution of sulfuryl chloride (25 g) in methylene chloride (300 mL) at −30° C. over a period of 30 min. The resulting mixture was stirred for 30 min at −30° C.; followed by the slow addition of triethylamine (76 g) at −30° C. and the reaction mixture was maintained for 60 minutes at the same temperature. The reaction mixture temperature was then raised to room temperature and the reaction was quenched with water (500 mL). The aqueous layer was separated and extracted twice with methylene chloride (2×200 mL). The combined organic layer was concentrated under reduced pressure to afford a residue that was subsequently dissolved in isopropyl alcohol (1940 mL) at 65°-70° C. The solution was allowed to cool to room temperature and stirred for 30 min. The resultant solid was filtered, washed with isopropyl alcohol (150 mL) and dried at 50-55° C. in a hot air oven to afford 2-amino-3-benzoyl-α-(methylthio)phenylacetamide (26 g) as a yellow solid.

Example-2

Preparation of Nepafenac

To a solution of 2-amino-3-benzoyl-α-(methylthio)phenylacetamide (26 gm) in tetrahydrofuran (340 mL) and water (80 mL), Raney nickel (wet 208 g) was added at room temperature. The mixture was stirred for 15 min and filtered through a hyflo bed. The filtrate was concentrated under reduced pressure and the obtained solid was dissolved in isopropyl alcohol (780 mL) at about 75°-80° C. The solution was allowed to cool to room temperature and the resultant precipitate was filtered and dried at about 50-55° C. under reduced pressure to afford nepafenac as a yellow solid (13 g).

Example 3

Purification of Nepafenac

To a solution of nepafenac (17 g) containing 0.33% of 2-amino-3-benzoyl-5-chlorobenzeneacetamide in methanol (2550 mL) was added potassium carbonate (17 g) and 10% palladium on carbon (1.7 g). Hydrogen gas was then applied to the mixture at about 40-45° C. and 5-7 psi pressure for about 8-10 hours. After completion, the reaction mass was filtered and the filtrate was concentrated to afford nepafenac with 0.06% 2-amino-3-benzoyl-5-chlorobenzeneacetamide. This product was further purified by crystallization from an isopropanol-water mixture (9:1) to afford nepafenac as a yellow solid (8.0 g, purity 99.86% with 0.03% 2-amino-3-benzoyl-5-chlorobenzeneacetamide).

Example 4

Purification of Nepafenac

To a solution of nepafenac (0.50 g) containing 0.67% of 2-amino-3-benzoyl-5-chlorobenzeneacetamide in methanol (75 mL) was added potassium carbonate (0.50 mg) and 10% palladium on carbon (50 mg). Hydrogen gas was then applied to the mixture at about 40-45° C. and 5-7 psi pressure for 12-13 hours. After completion, the reaction mass was filtered and the filtrate was concentrated to afford nepafenac with 0.08% 2-amino-3-benzoyl-5-chlorobenzeneacetamide. This product was further purified by crystallization from an isopropanol-water mixture (9:1) to afford nepafenac as a yellow solid (0.3 g, purity 99.84%, with 0.03% 2-amino-3-benzoyl-5-chlorobenzeneacetamide).

Example 5

Purification of Nepafenac

To a solution of nepafenac (17 g) containing 0.33% 2-amino-3-benzoyl-5-chlorobenzeneacetamide in methanol (2550 mL) was added triethylamine (17 g) and 10% palladium on carbon (1.7 g). Hydrogen gas was then applied to the mixture at about 40-45° C. and 5-7 psi pressure for 8-10 hours. After completion, the reaction mass was filtered and the filtrate was concentrated to afford nepafenac (yield 11 g, purity 99.86% with 0.06% 2-amino-3-benzoyl-5-chlorobenzeneacetamide).

Example 6

Purification of Nepafenac

To a solution of nepafenac (1 g) containing 0.67% 2-amino-3-benzoyl-5-chlorobenzeneacetamide in methanol (150 mL) was added triethylamine (1 g) and 10% palladium on carbon (100 mg). Hydrogen gas was then applied to the mixture at about 40-45° C. and 5-7 psi pressure for 8-10 hours. After completion, the reaction mass was filtered and the filtrate was concentrated to afford nepafenac (yield 0.67 g, purity 99.89% with 0.01% 2-amino-3-benzoyl-5-chlorobenzeneacetamide).

We claim:

1. A process for the preparation of nepafenac, comprising:
   a) treating 2-aminobenzophenone (II) with 2-(methylthio)acetamide (III) in the presence of sulfuryl chloride and a base to afford 2-(2-amino-3-benzoylphenyl)-2-(methylthio)acetamide (IV), and
   b) removing the thiomethyl moiety from the 2-(2-amino-3-benzoylphenyl)-2-(methylthio)acetamide (IV) to afford nepafenac.

2. The process of claim 1, wherein the removing of the thiomethyl moiety is conducted under reducing conditions.

3. The process of claim 2, wherein the reducing conditions comprise a hydrogen source and a catalyst.

4. The process of claim 3, wherein the catalyst is Raney nickel, palladium on carbon, palladium oxide, or platinum oxide.

5. The process of claim 4, wherein the reducing conditions further comprise a solvent selected from the group consisting of diethyl ether, tetrahydrofuran, and diisopropylether and the hydrogen source is hydrogen gas.

6. The process of claim 1, wherein the base is a trialkylamine, a dialkylamine, a cycloamine, or an N-alkylcycloamine.

7. The process of claim 6, wherein the base is selected from the group consisting of: triethylamine, diisopropylamine, methylisopropylamine, N-methylmorpholine and mixtures thereof.

8. The process of claim 7, wherein the treating of 2-aminobenzophenone (II) with 2-(methylthio)acetamide (III) occurs in a solvent selected from the group consisting of dichloromethane, dichloroethane, chloroform, diethyl ether, tetrahydrofuran, diisopropylether and mixtures thereof.

9. A process for the purification of a nepafenac composition containing a halogenated impurity, comprising: subjecting a nepafenac composition containing a halogenated impurity to reducing conditions, wherein the reducing conditions convert the halogenated impurity to nepafenac, and optionally crystallizing the resultant nepafenac composition.

10. The process of claim 9, wherein the halogenated impurity is 2-amino-3-benzoyl-5-chlorobenzeneacetamide.

11. The process of claim 10, wherein the reducing conditions comprise a hydrogen source and a catalyst.

12. The process of claim 11, wherein the catalyst is Raney nickel, palladium on carbon, palladium oxide, or platinum oxide.

13. The process of claim 12, wherein the reducing conditions further include a base.

14. The process of claim 13, wherein the base is selected from the group consisting of sodium hydroxide, potassium hydroxide, sodium carbonate, potassium carbonate, diisopropylamine, methylisopropylamine and triethylamine and the hydrogen source is hydrogen gas.

15. The process of claim 9, wherein the resultant nepafenac composition is crystallized and the crystallization is performed in a solvent comprising an alcohol.

16. The process of claim 15, wherein the alcohol is methanol, ethanol, isopropanol or mixtures thereof.

17. The process of claim 9, wherein the resultant nepafenac is crystallized from an isopropanol-water (9:1) mixture.

18. A process for the preparation of 2-(2-amino-3-benzoylphenyl)-2-(methylthio)acetamide (IV), comprising: treating 2-amino-benzophenone (II) with 2-(methylthio)-acetamide (III) in the presence of sulfuryl chloride and a base to afford 2-(2-amino-3-benzoylphenyl)-2-(methylthio)acetamide (IV).

19. The process of claim 18, wherein the base is a trialkylamine, a dialkylamine, a cycloalkylamine or an N-alkylcycloamine.

20. The process of claim 18, wherein the base is an organic amine.

* * * * *